US011077005B1

(12) United States Patent
Economopoulos et al.

(10) Patent No.: US 11,077,005 B1
(45) Date of Patent: Aug. 3, 2021

(54) PATIENT ISOLATION SYSTEM AND METHOD

(71) Applicant: DUKE UNIVERSITY, Durham, NC (US)

(72) Inventors: Konstantinos Economopoulos, Durham, NC (US); Eric Richardson, Durham, NC (US); W. Neal Simmons, Durham, NC (US); Theresa Thompson, Durham, NC (US); Benjamin Wesorick, Durham, NC (US); Kanishka Patel, Durham, NC (US); Maximilian Sondland, Durham, NC (US); Dimitrios Bailas, Durham, NC (US); Shikha Sharma, Durham, NC (US); Paul Fearis, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 17/028,417

(22) Filed: Sep. 22, 2020

Related U.S. Application Data

(60) Provisional application No. 63/005,751, filed on Apr. 6, 2020, provisional application No. 63/020,765, filed on May 6, 2020.

(51) Int. Cl.
*A61G 10/02* (2006.01)
*A61B 42/10* (2016.01)
(Continued)

(52) U.S. Cl.
CPC ............ *A61G 10/023* (2013.01); *A61B 42/10* (2016.02); *A61B 46/40* (2016.02); *A61B 50/20* (2016.02);
(Continued)

(58) Field of Classification Search
CPC ............... A61G 10/005; A61G 10/023; A61G 10/00–04; A61B 11/00–009; G01L 7/06–088; G01L 7/02
See application file for complete search history.

(56) References Cited

U.S. PATENT DOCUMENTS 3,492,987 A   2/1970   Parker
6,418,392 B1  7/2002   Paschal, Jr.
(Continued)

FOREIGN PATENT DOCUMENTS

WO   WO-2018165715 A1 * 9/2018 ........... A61G 10/005

OTHER PUBLICATIONS

Ufimtseva, E., et al., "*Mycobacterium tuberculosis* shape and size variations in alveolar macrophages of tuberculosis patients," European Respiratory Journal, 2019, Abstract only.
(Continued)

*Primary Examiner* — Catherine B Kuhlman
(74) *Attorney, Agent, or Firm* — Polsinelli PC; Michelle L. McMullen; Rebecca C. E. McFadyen

(57) ABSTRACT

A portable, protective enclosure for coupling to a patient support includes a collapsible frame, a canopy drape, a pair of gloves and sleeves configured for receiving hands and arms of a user, and a zipper disposed along one of the side surfaces of the drape, wherein the side surface is not folded about itself when the zipper is in an open state. A pair of filters are disposed on opposing sides of one of the side surfaces of the canopy drape, the filters together providing high efficiency particulate air filtration for at least 99.97% of airborne particulate 0.3 microns in diameter. Gas-permeable media is provided for air intake. A fan in communication with the first and second filters is provided for creating negative pressure in the internal region of the canopy drape,
(Continued)

Figure 1:
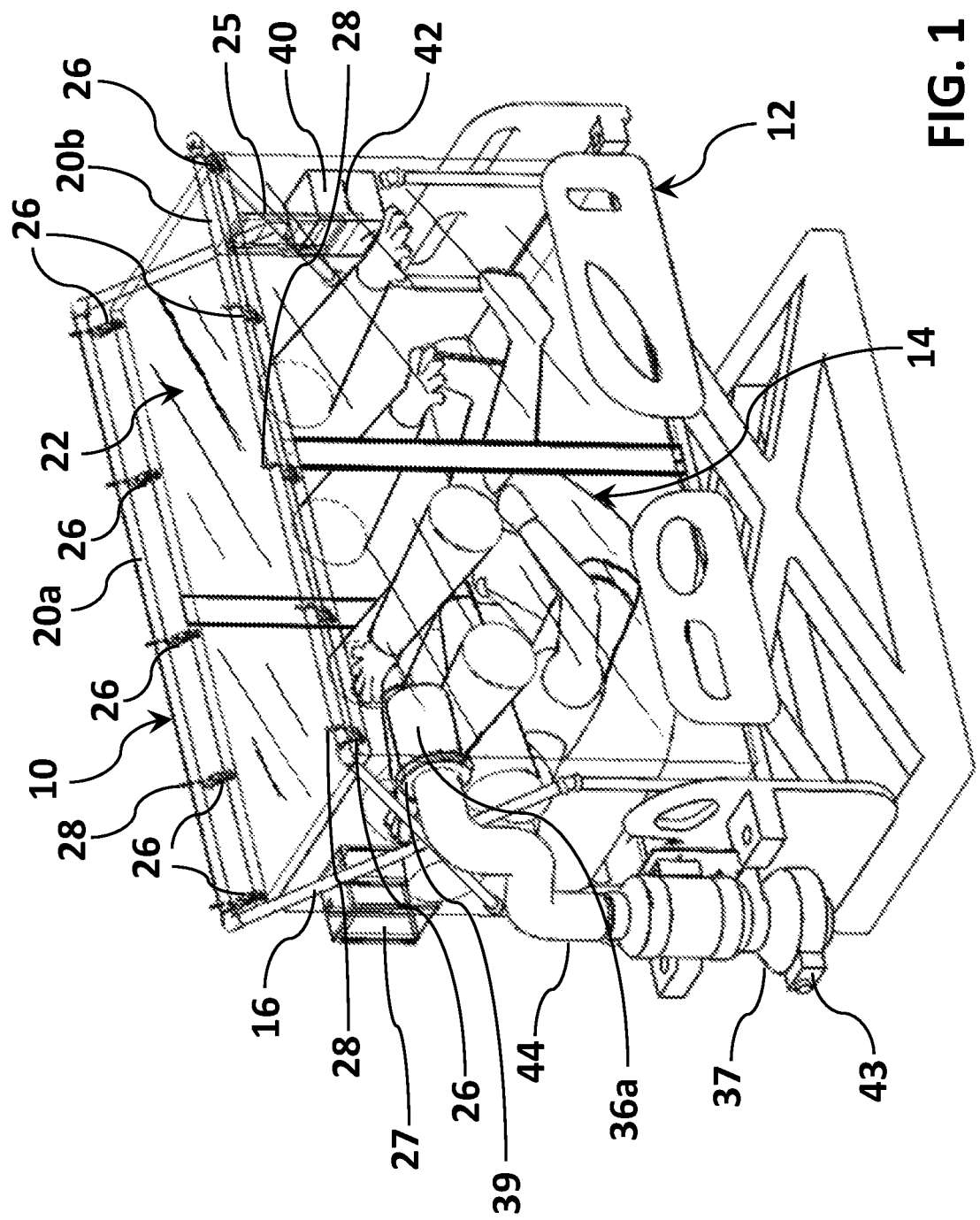
Figure 2:
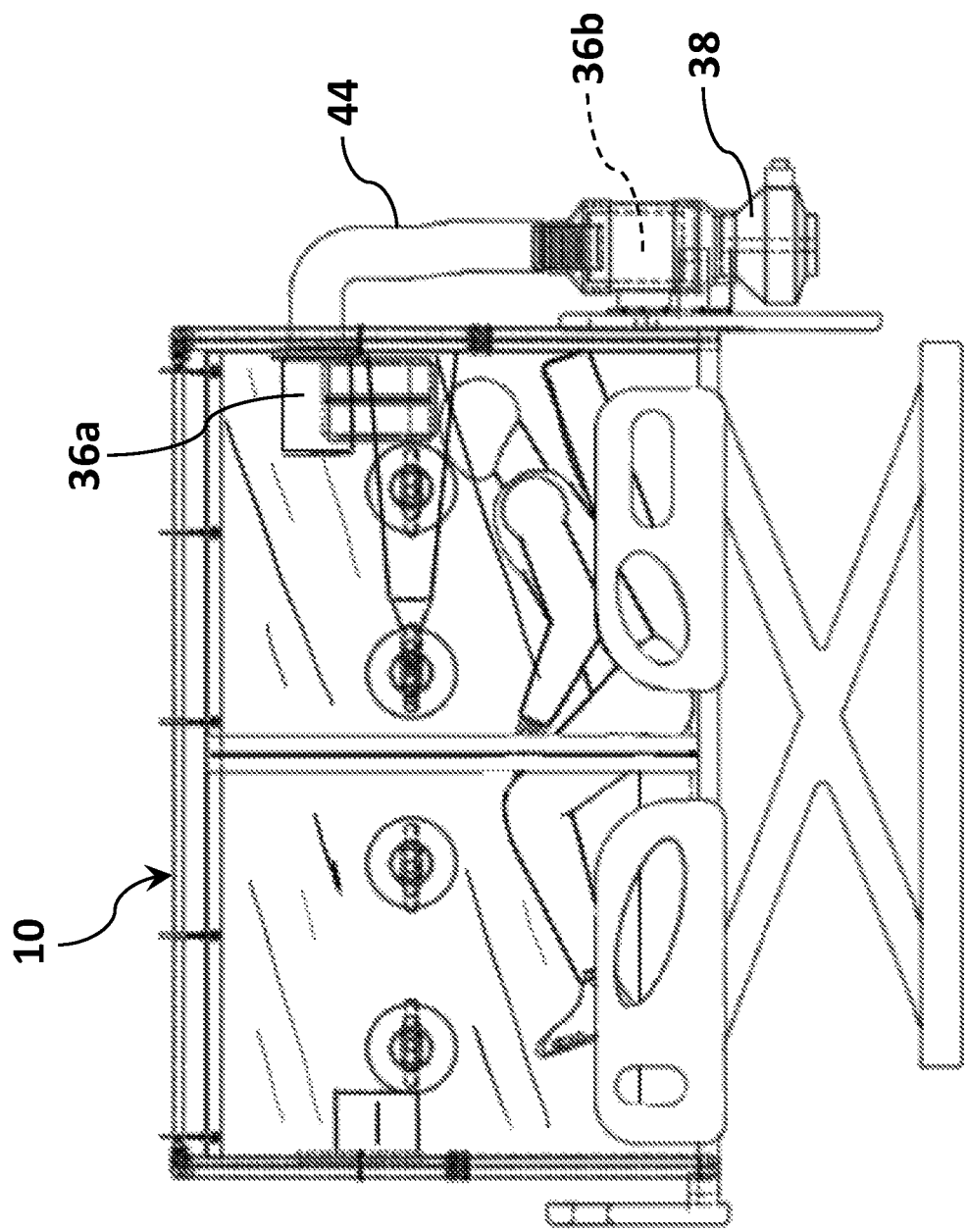
Figure 3:
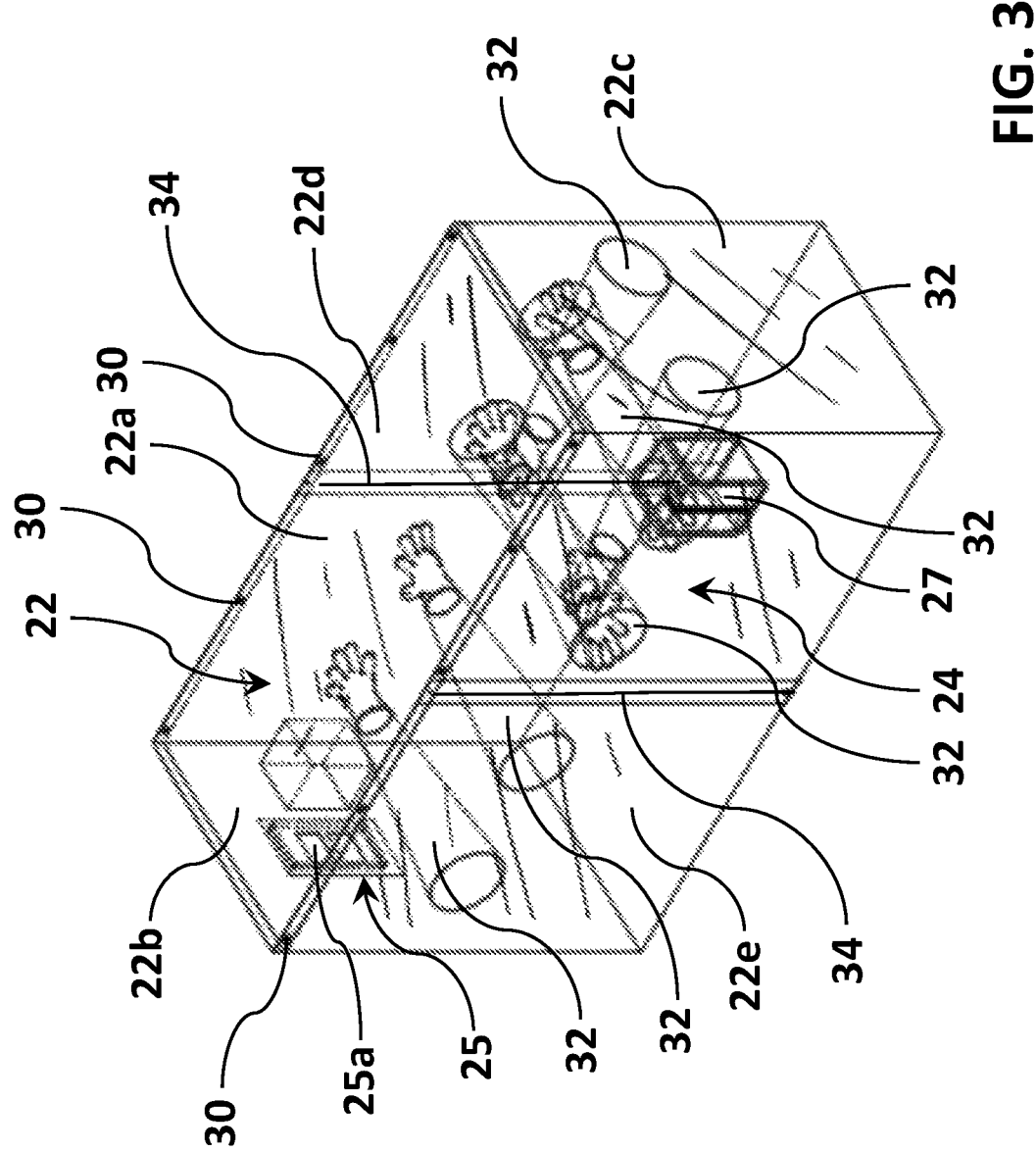
Figure 4:
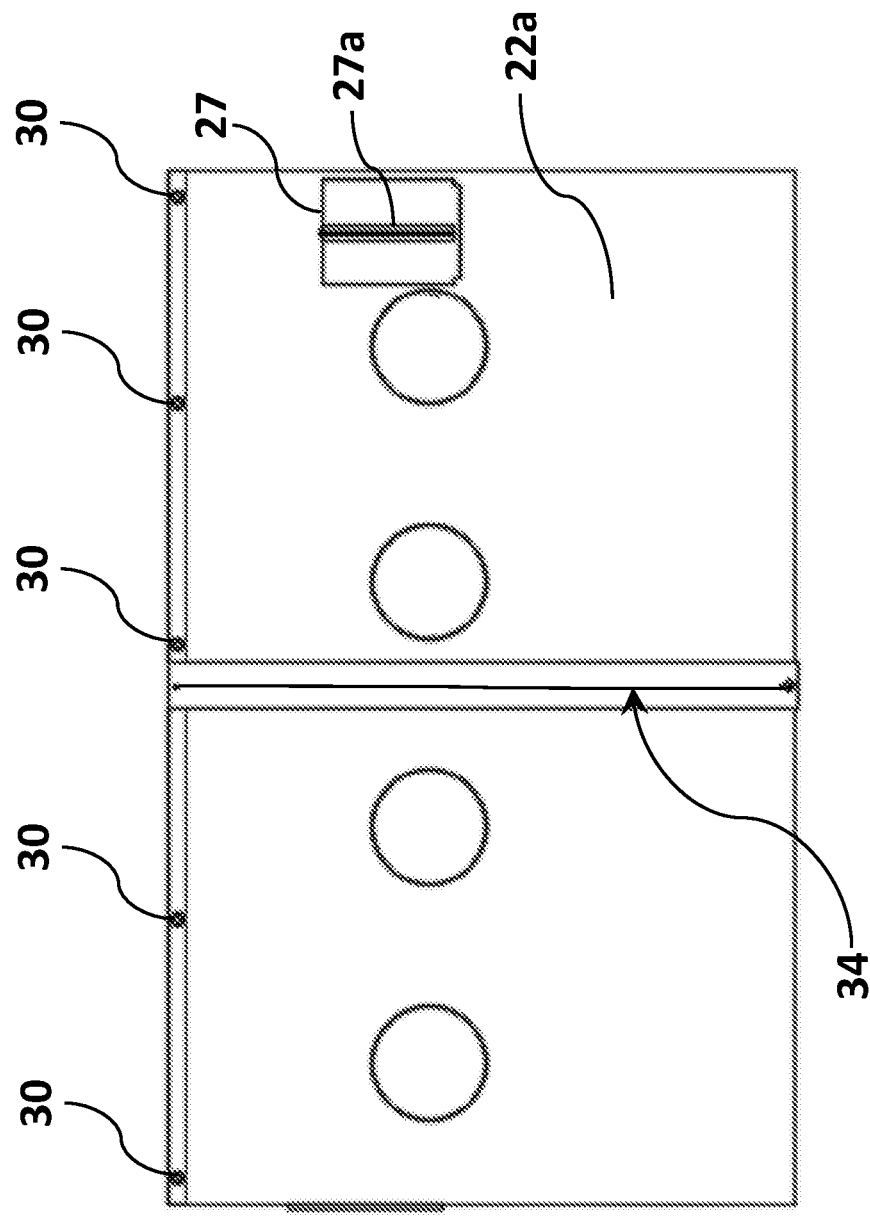
Figure 5:
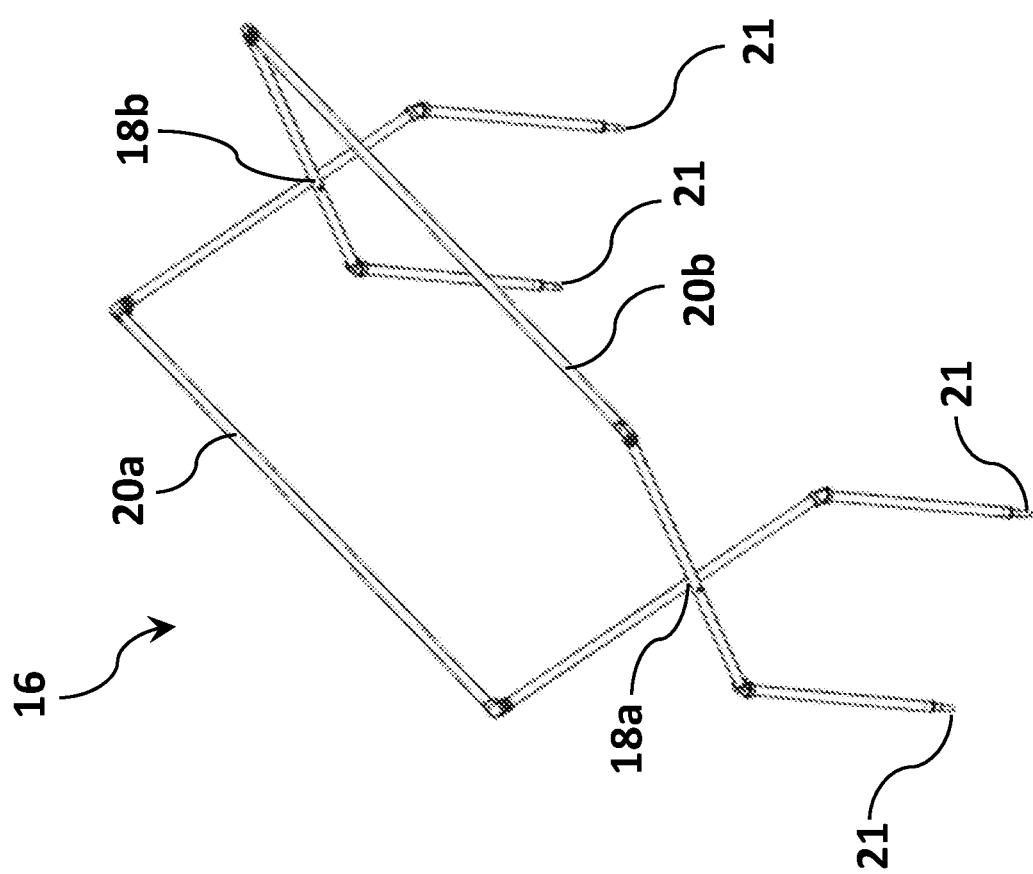
Figure 7:
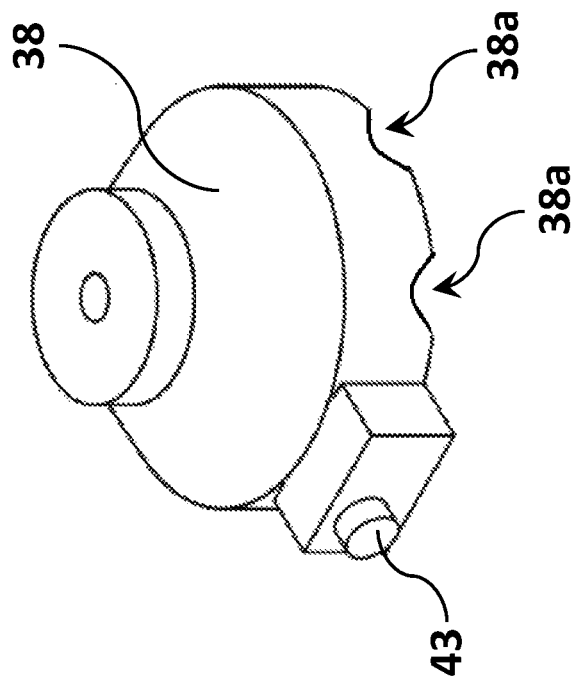
Figure 6:
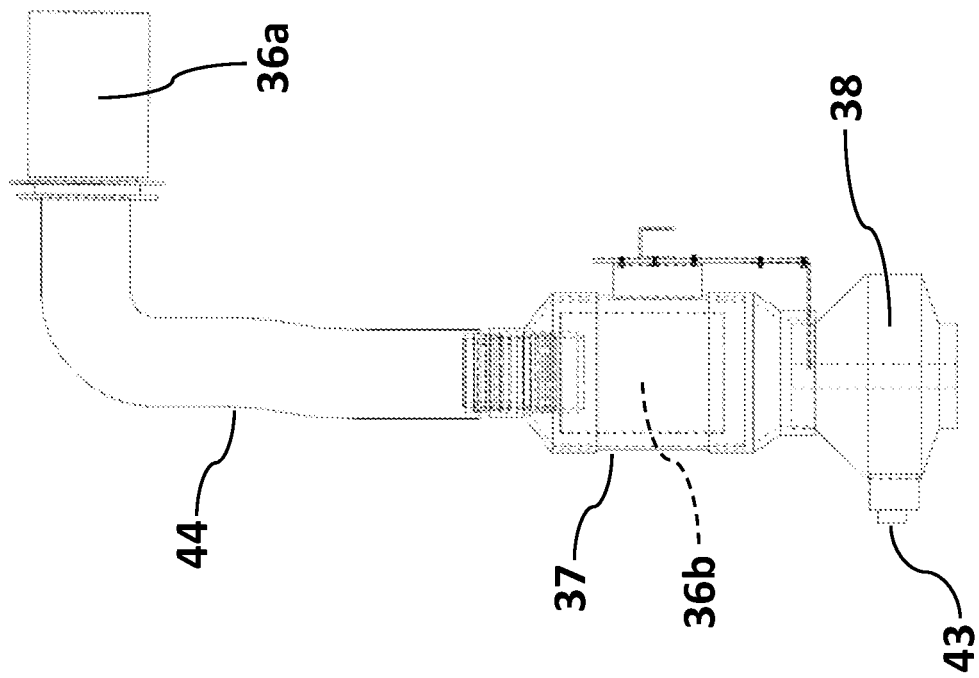
Figure 8:
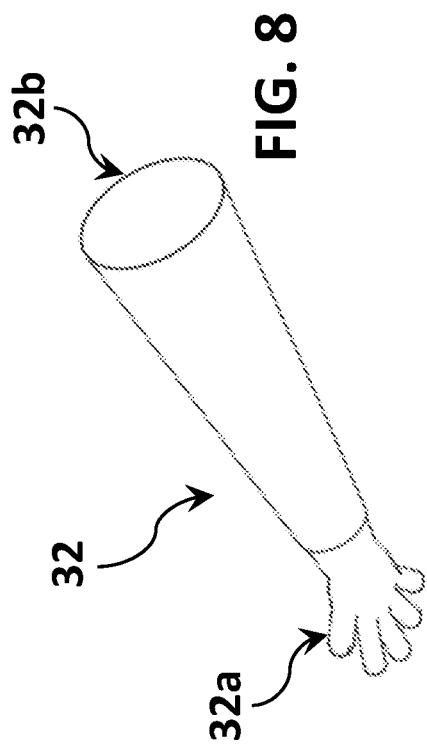

the fan configured to evacuate air from the internal region. A negative pressure indicator also is included.

15 Claims, 9 Drawing Sheets

(51) Int. Cl.
    *A61B 50/20*     (2016.01)
    *A61G 10/00*     (2006.01)
    *A61B 46/00*     (2016.01)
(52) U.S. Cl.
    CPC ........ *A61G 10/005* (2013.01); *A61G 2203/34* (2013.01)

(56) References Cited

U.S. PATENT DOCUMENTS

| | | | |
|---|---|---|---|
| 6,418,932 B2 | 7/2002 | Paschal, Jr. et al. | |
| 7,479,103 B2* | 1/2009 | Ellen | A47C 21/08 600/21 |
| 10,842,697 B1* | 11/2020 | Comunale | A61G 7/05 |
| 2010/0101198 A1* | 4/2010 | Phillips | B08B 15/02 55/385.2 |
| 2019/0388290 A1* | 12/2019 | Comunale | A61G 10/005 |

OTHER PUBLICATIONS

Hinton, D.M., Letter of Authorization, U.S. Food and Drug Administration (FDA), May 1, 2020.
Zhu, Na, et al., "A Novel Coronavirus from Patients with Pneumonia in China, 2019," The New England Journal of Medicine, vol. 382, pp. 737-733, 2020.
Ather, Binish, et al., "Airborne Precautions," NCBI Bookshelf, retrieved from the internet at <https://www.ncbi.nlm.nih.gov/books/NBK531468/?report=printable>, retrieved on Aug. 17, 2020.
Han, Z.Y., et al., "Characterizations of particle size distribution of the droplets exhaled by sneeze," Journal of The Royal Society, vol. 10, pp. 1-11, 2013.
Hsiao, Ta-Chih, et al., "COVID-19: An Aerosol's Point of View from Expiration to Transmission to Viral-mechanism," Aerosol and Air Quality Research, vol. 20, pp. 905-910, 2020.
Velayati, A.A., et al., "Morphological Characterization of *Mycobacterium tuberculosis*," Understanding Tuberculosis —Deciphering the Secret Life of the Bacilli, Chapter 8, 2012.
Savion Industries—Medical equipment, Isolation Stretchers, retrieved from the internet at <https://savion.co.il/#!isolation>, retrieved on Jul. 24, 2020.
Medica Magazine, Savion Industries Ltd., "Savion isolation products for ebola," 2014.
U.S. Department of Energy, "Specification for HEPA Filters Used by DOE Contractors," Distribution Statement, DOE-STD-3020-2015, Jun. 2015.
Perry, J.L., et al., "Submicron and Nanoparticulate Matter Removal by HEPA-Rated Media Filters and Packed Beds of Granular Materials," National Aeronautics and Space Administration, NASA/TM-2016-218224.
Johnson, G. R., et al., "The mechanism of breath aerosol formation," Journal of Aerosol Medicine and Pulmonary Drug Delivery, vol. 22(3), pp. 229-237, 2009.
Nascent Surgical, LLC "A Novel Method for Protection of the Corona Virus Healthcare Worker," retrieved from the internet at <http://nascentsurgical.com/viral-aerosol/>, retrieved on Sep. 2, 2020.
Business Wire "FDA Approves Emergency Use of A&R Tarpaulins' Patient Isolation Transportation Unit (PITU)," retrieved from the internet at <https://www.businesswire.com/news/home/20200520005264/en/FDA-Approves-Emergency-AR-Tarpaulins%E2%80%99-Patient-Isolation>, retrieved on Sep. 2, 2020.
Ather B, et al., "Airborne Precautions," Treasure Island (FL): StatPearls Publishing; Jan. 2021; https://www.ncbi.nlm.nih.gov/books/NBK531468/.
Han ZY, et al., "Characterizations of particle size distribution of the droplets exhaled by sneeze," 2013, J R Soc Interface, 10: 20130560.
Hsiao TC, et al., "COVID-19: An Aerosol's Point of View from Expiration to Transmission to Viral-mechanism," 2020, Aerosol Air Qual. Res., 20: 905-910.
Johnson GR, et al., "The Mechanism of Breath Aerosol Formation," 2009, J Aerosol Med Pulm Drug Deliv., 22: 229-237.
Perry JL, et al., "Submicron and Nanoparticulate Matter Removal by HEPA-Rated Media Filters and Packed Beds of Granular Materials." NASA/TM-2016-218224; National Aeronautics and Space Administration.
Ufimtseva E, et al., *Mycobacterium tuberculosis* shape and size variations in alveolar macrophages of tuberculosis patients, 2019, European Respiratory Journal, 54(Suppl. 63): PA4605.
Velayati AA, et al., "Morphological Characterization of *Mycobacterium tuberculosis* in Understanding Tuberculosis—Deciphering the Secret Life of the Bacilli," Pere-Joan Cardona (Ed.). Intech (Rijeka, Croatia), pp. 149-166.
Zhu N, et al., "A Novel Coronavirus from Patients with Pneumonia in China," 2019, N Engl J Med., 382(8):727-733.

* cited by examiner

PATIENT ISOLATION SYSTEM AND METHOD

CROSS REFERENCE TO RELATED APPLICATIONS

This application claims the benefits of U.S. Provisional Application No. 63/005,751 filed Apr. 6, 2020 by Konstantinos Economopoulos et al. and entitled "Patient Isolation Chamber" as well as U.S. Provisional Application No. 63/020,765 filed May 6, 2020 by Konstantinos Economopoulos et al. and entitled "Patient Isolation Tent" under 35 U.S.C. § 119(e) and the entire contents of these applications are expressly incorporated herein by reference thereto.

FIELD OF THE INVENTION

The invention relates to enclosure systems and methods for isolating subjects during medical admissions, assessment, treatment, transportation, and other environments. More particularly, the invention relates to protective enclosure systems and methods for protecting health care professionals ("HCP"), and vulnerable populations such as immunocompromised patients, from direct exposure to contagions infecting subjects, for example, communicable diseases that may spread through physical contact or travel through the air such as the coronavirus disease COVID-19 (i.e. SARS-CoV-2). Even more particularly, the invention relates to a low-cost, modular, portable, negative-pressure or positive-pressure isolation chamber with air filtration meeting a high-efficiency particulate air ("HEPA") standard by filtering at least 99.97% of any airborne particles with a size of 0.3 microns ($\mu$m).

BACKGROUND

The worldwide pandemic associated with the coronavirus disease, COVID-19, laid bare an immense need in medical environments for systems and methods to minimize contamination of the environment by pathogens and to protect HCP from infection during transportation and hospitalization of infectious patients.

Highly infectious diseases, e.g., COVID-19 among other pathogens such as *Mycobacterium tuberculosis*, involve rapid and widespread transmission. Experience has demonstrated that medical transports and subject-receiving facilities can face nearly exponential and overwhelming demand for services from infected patients. Experience also has demonstrated that such a sudden spike severely taxes supply chains for personal protective equipment ("PPE"), medical filters, and other medical supplies, creating shortages that increase risk of infection for HCP who, of necessity, are in close proximity to infected subjects. In addition, experience has further demonstrated that the economic upheaval accompanying a pandemic requires careful consideration of all costs within the healthcare system. Traditional business models for operating medical facilities can become unsustainable at least in the short-term. This is especially due to disruptions in conducting elective surgeries, challenges presented by underinsured patient populations, and importantly, the scarcity of PPE, ventilators, medical filters, and other medical supplies. As for the latter, scarcity of such products coupled with massive demand can result in substantial price increases. In short, especially during a pandemic, those managing the health care system need to watch every dollar spent and engage in uncomfortable decision-making about what can be afforded. During pandemics, hospitals especially need to rely on innovation to address potential medical supply shortages.

It is not easy to anticipate or effectively respond to the financial upheavals that occur during a pandemic, but it is vital, nevertheless. Coupled with an overwhelming demand, larger underinsured patient populations, disruptions in elective surgery schedules, and the scarcity of PPE altogether can result in substantial price increases. Robust logistical strategies for triaging and providing quality care with limited supplies must therefore be developed. Thus, cost-effective, innovative approaches and solutions are needed to address the unusual and urgent circumstances occasioned by pandemics.

On May 1, 2020, the U.S. Food and Drug Administration (FDA) issued an Emergency Use Authorization (EUA) for protective barrier enclosures in response to the evolving COVID-19 pandemic and concerns relating to the transmission of the virus during patient care. The EUA specified: "A protective barrier enclosure is a transparent device designed to cover a patient's head and upper body that incorporates one or more ports through which the HCP's hands are passed to perform medical procedures. It does not include fans, air filters, or other features and is not intended to generate negative pressure." The EUA recognized a need for protective barrier enclosures that "prevent HCP exposure to pathogenic biological airborne particulates by providing an extra layer of barrier protection in addition to personal protective equipment (PPE)." The FDA also stated in the EUA: "Currently, there are no FDA-cleared or approved barrier protection devices that are available for use by HCPs when caring for or performing medical procedures on patients who are known or suspected to have COVID-19 in healthcare settings to prevent HCP exposure to pathogenic biological airborne particulates."

The May 1, 2020 EUA does not cover more advanced protective barrier enclosures that operate under a negative pressure gradient and/or provide high efficiency particulate filtration of airborne particles from the air in the enclosures. Thus, use of such systems involves a separate authorization from the FDA, which must be sought for a particular design.

Protective barrier enclosures were clinically used at a large scale outside the United States during the 2014 Ebola outbreak. A non-FDA-approved, commercial product announced by Savion Industries in 2014 was a "Galileo Ebola Bed" fitted with an isolation chamber. As disclosed, a transparent isolation chamber completely covered the bed surface to a height that enabled a patient to be seated inside. A battery-operated pump attached to the chamber through a replaceable carbon filter and created a chamber of negative pressure into which uncontaminated air flowed from the environment. The chamber was fitted with conduit openings and sleeves on both sides.

Among Savion's products is a portable Mobile Compact Isolation Chamber (model MCC700) "designed for ambulance stretcher, hospital beds and stretchers for transportation in ambulances and inside hospitals" that includes a two stage Nuclear, Biological and Chemical (NBC) filter for contaminated air from the chamber. Savion also offers a pediatric isolation chamber crib (model PIC 436) that provides access to the chamber for up to three caregivers through replaceable conduit sleeves, and through conduits.

U.S. Pat. No. 3,492,987 to Parker is directed to an "Isolation Apparatus" and discloses an enclosure member surrounding a patient disposed in a prone position on a mattress and bedding of a hospital type bed. The enclosure member is held in an essentially box-like configuration by a support assembly. The enclosure member is formed of an integral body of skin or sheet material inclusive of a bottom portion, upright side and end wall portions, and top portions interconnected at their ends in a hermetically sealed enclosure in a box-like configuration. The bottom portion of the enclosure member is under the mattress, so the entire mattress is fully enclosed. Glove members are provided in the side walls for arm insertion into the enclosure to manipulate objects within the enclosure member from externally thereof. Material suitable for forming the enclosure member is disclosed as thin, transparent plastic material, and the patent discloses that the glove members may also be formed of a similar material. A sealed pass receptacle or box is disposed at one end of the enclosure member. The support assembly is collapsible. The side wall portion has a slide fastener assembly of the zipper type for initial entry and final exit of the patient into and from the enclosure. In another embodiment, the enclosure member surrounds the entire bed and is disposed on the floor.

U.S. Pat. No. 6,418,932 B2 to Paschal, Jr. et al. is directed to a "Convertible Patient Isolation Pod." The patent discloses an emergency personal isolation and containment pod formed from plastic sheeting and in the form of an elongated tube which is split longitudinally to provide an essentially bifurcated shell defined by tube halves sized to facilitate patient introduction into and extrication from the pod by emergency personnel or other caregivers. The pod is depicted on a stretcher. A seam formed along the edges of the shell halves is a ZIP-LOC® type. The patent discloses that due to evacuation of air from the interior of the pod, a negative pressure can develop which would collapse the unsupported tube about a patient sealed therein, and consequently the use of a supporting frame is desirable. Air is positively directed through the pod by a portable electrically actuated blower with an intake port adapted for a filter cartridge. The filter cartridge comprises a HEPA or NBC (nuclear, biological, chemical) filter for removal of air contaminants in the nanometer range. To facilitate caregiver activities such as airway management and the like, the pod includes a plurality of ported isolation tear resistant gloves that include a reinforced portal and tubular sleeves to allow for patient treatment without exposure of the patient to the ambient.

U.S. Pat. No. 7,479,103 B2 to Ellen is directed to a "Portable Isolation Enclosure" and discloses a collapsible enclosure that would be used in a hospital environment with a standard hospital bed. The enclosure has a unitary aluminum frame. A canopy is draped about the frame. The canopy defines an isolation chamber for receiving a patient that is sealed with respect to the ambient atmosphere, and is self-contained (i.e., the sealed enclosure is defined entirely by the canopy and is not defined by, for example, the floor or other external surface). An environmental control device is connectable in fluid communication with the isolation chamber and includes (i) a filter adapted to at least one of filter air entering and filter air exiting the isolation chamber, and (ii) a pump adapted to at least one of pump air into the isolation chamber to increase the pressure within the isolation chamber relative to the ambient atmosphere, and pump air out of the isolation chamber to decrease the pressure within the isolation chamber relative to the ambient atmosphere. The patent discloses use of a "HEPA" or other suitable filtration system. The canopy defines a plurality of glove ports to allow a physician, other care giver or individual access to the patient and/or isolation chamber.

U.S. Patent Application Publication No. US 2019/ 0388290 A1 is directed to a "Disposable Bio-Secure Environmental Unit" and discloses a bio-disposable environmental transport that includes a containment tent positioned and secured in place on top of a gurney, stretcher, hospital bed, or other structure. A rigid frame is provided for the containment tent. The containment tent is bio-disposable with a 20 mil clear poly plastic floor, walls, and ceiling and is easily secured onto the frame. An integrated pass through isolation pouch is provided for moving supplies into, and out from, the containment tent. Also incorporated is an integrated battery powered negative or positive pressure ventilation system with HEPA filtered exhaust. A large zippered patient entry door with Velcro® seal folds downward when open to protect the stretcher and containment tent and environmental unit during patient entry and exit. Multiple integrated sealed port glove access are provided for patient care processes. The gurney, already prepared with an environmental unit, is opened by: downwardly unzipping each zipper located on the right and left side of the isolation gurney; grabbing the Velcro® located at the top of the environmental unit and pulling the Velcro® apart and allowing the isolation unit closure to fall downward.

Despite these developments, there remains a need for an improved, low-cost, modular, portable, negative-pressure or positive pressure patient isolation system and method, providing a chamber with air filtration at least meeting a high-efficiency particulate air ("HEPA") standard, and in some embodiments meeting an Ultra-Low Particulate Air ("ULPA") standard, with respect to airborne particles. There especially remains a need for systems and methods that can isolate a patient and provide air filtration meeting the HEPA and/or ULPA standard but without the use of commercial HEPA and/or ULPA rated filters, whose availability can be scarce during a pandemic. In other words, there is a need for filtration achieved using commercial non-HEPA and/or non-ULPA filters that nevertheless may achieve HEPA-level and/or ULPA-level filtration (e.g., multiple non-HEPA rated filters disposed serially with respect to each other). There also remains a need for such isolation systems and methods in which isolation chambers can be readily deployed to surround a patient on a support, and rapidly removed from the patient support if medical judgment deems it necessary. Such a need exists with respect to isolation chambers that are used both in transport as well as potentially long-term hospitalizations. In addition, there is a need for patient isolation systems and methods employing chambers that in particular provide a "bottomless" canopy that merely abuts the sides of a patient support while permitting a negative pressure to be maintained therein. In other words, a mechanical seal—whether by clamping or otherwise—is not needed between the canopy and patient support to achieve sufficient negative pressure within the isolation chamber. Still further, there exists a need for systems and methods that employ a combination of reusable and disposable components, such as a reusable frame and disposable plastic sheeting forming the canopy drape. With a substantial influx of infectious patients to medical facilities such as during a pandemic, there can be a pressing need for systems and methods for isolating patients in chambers coupled to stretchers, beds, wheelchairs, and other patient supports.

SUMMARY

An isolation tent can be temporarily disposed over a hospital bed or gurney. The isolation tent can optionally include a negative-pressure ventilation or filtration system.

A portable protective enclosure for coupling to a patient support for supporting a mammal may include a collapsible frame having a pair of X-shaped linkages coupled with a pair of cross-members and a canopy drape. The canopy drape may be formed of a transparent, first polymeric material, the canopy drape being bottomless and having a top surface, a plurality of side surfaces, an internal region disposed between the top and side surfaces, an air intake portion, and a first thickness, wherein the canopy drape may be coupled to at least one of the cross-members. A pair of sleeves and gloves may be configured for receiving hands and arms of a user such as a HCP, the sleeves and gloves together having a closed, first free end, an open, second free end, and a second thickness, wherein the sleeves are coupled to the canopy drape to form an air-tight seal therebetween and the second thickness is less than the first thickness.

A zipper may be disposed along one of the side surfaces, the zipper having a closed state and an open state, wherein the side surface is not folded about itself when the zipper is in the open state. In addition, a first filter may be disposed in communication with a second filter, the first and second filters disposed on opposing sides of one of the side surfaces of the canopy drape, wherein the first and second filters together provide high efficiency particulate air filtration to filter at least 99.97% of airborne particulate of 0.3 µm in diameter. Gas-permeable media, which in some embodiments may be a polymeric filter, may be disposed in communication with and proximate the air intake portion A movable fan may be provided in communication with the first and second filters for creating negative pressure of at least 0.01 inches of water, and in some embodiments at least 0.02 inches of water, in the internal region of the canopy drape, the fan being configured to draw in air through the gas-permeable media, into the internal region and evacuate air from the internal region through the first and second filters. Still further, a negative pressure indicator may be included.

In a preferred, exemplary embodiment, the first polymeric material is a transparent thermoplastic polyurethane and the first thickness is about 10 mils. At least one of the sleeves and the gloves may be formed of a second polymeric material. The second polymeric material may be thermoplastic polyurethane and transparent. The second thickness may be about 2 mils. The sleeves may be coupled to the canopy drape by a coupling selected from the group consisting of welds, bonds, or mechanical connections. The coupling may further include seam tape. A plurality of grommets may be disposed proximate the top surface of the canopy drape. The canopy drape may be coupled to both of the cross-members. The fan may provide a flow rate of air from the internal region of the canopy drape of between about 70 cfm and about 100 cfm. The fan may be adapted to create a negative pressure of at least 0.01 inches of water, and in some embodiments 0.02 inches of water, in the internal region. The internal region may have a volume of between about 25 cubic feet and about 125 cubic feet. In addition, the negative pressure indicator may be an expandable vessel coupled to the canopy drape. In some embodiments, the expandable vessel may be a balloon. Also, in some embodiments, the expandable vessel may have indicia for indicating when desired pressure is reached, and the indicia may be a straight line or alternatively a geometric shape such as a rectangle, an image of a corporate logo, or an image of a university mascot. In a preferred embodiment, the indicia is two-dimensional. The expandable vessel may be formed of the second polymeric material. The expandable vessel may be sealingly coupled to a side surface of the canopy drape.

In some embodiments, the first polymeric material may be thermoplastic polyurethane, and the first thickness may be about 10 mils. The second polymeric material may be thermoplastic polyurethane, and have a second thickness that is about 2 mils. The first and second polymeric material each may be transparent.

The sleeves may be welded to the canopy drape. In some embodiments, the sleeves are heat welded to the canopy drape. In others, they may be bonded together. In still others, the enclosure may further include stitching, wherein the sleeves and the canopy drape are stitched to each other. Seam tape may be provided in contact with the stitching to create an air-tight seal.

A plurality of grommets may be disposed proximate the top surface of the canopy drape. An openable, spring-hinged connector may be coupled to each grommet and one of the cross-members. Each openable, spring-hinged connector may be coupled to the one of the cross-members with a zip tie. In a preferred embodiment, the drape may be coupled to both of the cross-members. The openable, spring-hinged connector may be a carabiner or a curtain ring.

The fan may provide a flow rate of air from the internal region of the canopy drape of between about 70 cubic feet per minute (cfm) and about 100 cubic feet per minute (cfm). Also, the internal region preferably may have a volume of between about 25 cubic feet and about 125 cubic feet. Alternatively, the internal region may have a volume of between about 25 cubic feet and about 75 cubic feet.

The negative pressure indicator may be an expandable vessel coupled to the canopy drape. The expandable vessel may be a balloon and may include indicia for indicating when desired pressure is reached. The indicia, for example, may be a line. The expandable vessel may be formed of the first or second polymeric material. The expandable vessel may be sealingly coupled to a side surface of the canopy drape.

In some embodiments, a compartment may be coupled to the canopy drape, the compartment having two openable portions.

In some embodiments, the first and second filters together may provide high efficiency particulate air filtration to filter at least 99.99% of airborne particulate of 0.3 µm in diameter.

A method of isolating a single mammal with a communicable disease may include: substantially enclosing the single mammal in an internal space defined between a support for the single mammal and a substantially transparent, polymeric barrier with an opening having gas-permeable media disposed therein; drawing air from an exterior space through the gas-permeable media to create a negative pressure of at least 0.01 inches of water in the internal space; monitoring the negative pressure with a passive indicator; disposing a first filter in the internal space, drawing the air through the first filter at a flow rate between 70 cfm and 100 cfm, and capturing microorganisms of the communicable disease therein, the microorganisms having a size between 20 nm and 5 µm; disposing a second filter in the exterior space downstream of the first filter and drawing the air passing through the first filter through a flexible conduit to the second filter and through the second filter, and further capturing additional microorganisms of the communicable disease therein; and exhausting the air downstream of the second filter to the exterior space. The barrier may hang freely proximate sides of the support.

The size may be measured in any dimension of the microorganism, such as an overall length, breadth, or diameter of the microorganism. For example, *Mycobacterium tuberculosis* is a curved rod measuring 0.2-0.5 µm by 2-4 µm.

The size of the microorganisms may be a diameter between 60 nm and 140 nm. The microorganisms may be coronavirus virions. The exhausted air may be substantially free of the microorganisms.

In some embodiments, the passive indicator expands, and orientation of indicia thereon changes, until the air creates the negative pressure of at least 0.01 inches of water in the internal space.

A method of isolating a single mammal with a communicable disease includes: substantially enclosing the single mammal in an internal space defined between a support for the single mammal and a substantially transparent, polymeric barrier with an opening having gas-permeable media disposed therein; drawing air from an exterior space through the gas-permeable media to create a negative pressure of at least 0.01 inches of water in the internal space; monitoring the negative pressure with a passive indicator; disposing a first filter in the internal space and drawing the air through the first filter at a flow rate between 25 cfm and 100 cfm and capturing virions of the communicable disease therein, the virions being generally spherical, pleomorphic, and having an average diameter between 60 nm and 140 nm; disposing a second filter in the exterior space downstream of the first filter and drawing the air passing through the first filter through a flexible conduit to the second filter and through the second filter, and further capturing additional virions of the communicable disease therein; exhausting the air downstream of the second filter to the exterior space. The exhausted air may be substantially free of the virions. In some embodiments, the barrier hangs freely proximate sides of the support. The passive indicator may expand, and orientation of indicia thereon may change, until the air creates the negative pressure of at least 0.01 inches of water in the internal space.

The virions may be coronavirus virions and may have spikes projecting therefrom by 9 nm to 12 nm. The virions may be SARS-CoV-2 virions.

The method may further include: removing the first filter from the internal space for laboratory analysis of pathogens including the virions collected therein. The method may further include: replacing the first filter with a substitute filter; as well as transferring the first filter and the substitute filter through a transfer chamber in communication with the barrier, the transfer chamber configured and dimensioned to generally restrict movement of the air therethrough, so that the negative pressure is maintained in the internal space during the transferring. The substitute filter may be transferred into the internal space before the first filter is removed from the internal space. The step of replacing the first filter with a substitute filter may occur before the first filter is removed from the internal space.

The virions of the communicable disease may be captured in the first filter and/or second filter while coupled to at least one carrier. Only two filters may be used to collect the virions between the internal space and the external space.

In some embodiments, the flow rate may be between 70 cfm and 100 cfm. In some embodiments, the flow rate may provide at least 30 air exchanges per hour from the internal space, at least 60 air exchanges per hour from the internal space, or at least 100 air exchanges per hour from the internal space.

The methods disclosed herein also may be used for other forms of particulate, not just microorganisms.

BRIEF DESCRIPTION OF THE FIGURES

Preferred features of the inventions are disclosed in the accompanying drawings, wherein:

FIG. 1 is a side perspective view of an exemplary patient isolation chamber disposed on a hospital bed;

FIG. 2 is a side view of the embodiment of the patient isolation chamber disposed on a bed of FIG. 1;

FIG. 3 is a side perspective view of the patient isolation chamber of FIG. 1;

FIG. 4 is a side view of the canopy drape of the patient isolation chamber of FIG. 1;

FIG. 5 is a side perspective view of the collapsible frame of the patient isolation chamber of FIG. 1;

FIG. 6 is a side view of the fan and filter system of the patient isolation chamber of FIG. 1;

FIG. 7 is a side perspective view of the fan subsystem of the patient isolation chamber of FIG. 1;

FIG. 8 is a side perspective view of the sleeve/glove of the patient isolation chamber of FIG. 1;

FIG. 9A is a side view of the negative pressure indicator of the patient isolation chamber of FIG. 1 in an uninflated state;

FIG. 9B is a side view of the negative pressure indicator in an inflated state within indicia in the form of a line;

FIG. 9C is another side view of the negative pressure indicator in an inflated state with indicia instead in the form of a geometric shape;

FIG. 10 is a side perspective view of a two-way transfer chamber for coupling to the patient isolation chamber of FIG. 1; and FIG. 11 is a side perspective view of the tubing that leads to the externally disposed fan coupled to the internally disposed filter of the patient isolation chamber of FIG. 1, with the tubing and filter shown in a de-coupled configuration for illustrative purposes.

DETAILED DESCRIPTION

As used herein, the terms "subject" and "patient" are used interchangeably and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like.

As used herein, the term "HEPA" refers to filtering that at least meets the U.S. Department of Energy (DOE) Technical Standard entitled "Specification for HEPA Filters Used by DOE Contractors," DOE-STD-3020-2015, June 2015, which defines a HEPA Filter as: "A throwaway, extended-medium, dry type filter with a rigid casing enclosing the full depth of the pleats. The filter shall exhibit a minimum efficiency of 99.97% when tested with an aerosol of 0.3 micrometer diameter."

As used herein, the term "ULPA" refers to filtering that removes 99.9995% (most penetrating particle size (MPPS) efficiency) of contaminants 0.12 μm or larger in diameter (U15 classification). See British Standards Institute standard BS EN 1822-1:2019, High efficiency air filters (EPA, HEPA and ULPA). Classification, performance testing, marking.

The coronavirus "SARS-CoV-2" (the virus itself) is also commonly known by, and at times referred to by the disease names "2019 novel coronavirus," "2019-nCoV," "coronavirus disease 2019," and "COVID-19" from the abbreviations corona ("CO") virus ("VI") disease ("D"), and all of the following virus and disease names are used interchangeably herein.

As used herein, the term "transparent" concerns the see through nature of the material, and specifically to the ability of a patient and/or HCP to see relatively clearly through the material so as to be able to discern people and/or objects on the other side thereof.

Unless otherwise defined, all technical terms used herein have the same meaning as commonly understood by one of ordinary skill in the art to which this disclosure belongs.

A tent can be placed around a patient's bed or stretcher in order to isolate the patient. The tent may be particularly useful, for example, for COVID-19 positive patients or patients with other infectious pathogens. The patient isolation chamber may minimize contamination of the environment by the pathogen and protect HCP from becoming infected during transportation of the patient, as well as during hospitalization of infectious patients. Advantageously, the patient isolation chamber may allow the earlier performance of ventilation procedures (e.g., BiPAP, CPAP, etc.) that are otherwise delayed in COVID-19 patients due to the excess production of aerosol particles.

The patient isolation chamber may provide an additional layer of protection between the patient and the HCP, family members, visitors, other patients, etc.

Turning to FIGS. 1-11, in a preferred exemplary embodiment, a portable protective enclosure 10 is provided for coupling to a patient support 12 (e.g., a hospital bed) for supporting a patient 14. A collapsible frame 16 is formed of a pair of X-shaped linkages 18a, 18b coupled with a pair of cross-members 20a, 20b. Posts 21 are configured and dimensioned to be inserted in receptacles in patient support 12 to demountably couple frame 16 to patient support 12. In alternate embodiments, frame 16 may be coupled to patient support 12 with brackets, clamps, or another mechanical connection.

A canopy drape 22 preferably is formed of a transparent, first polymeric material. Canopy drape 22 is bottomless and has a top surface 22a and a plurality of side surfaces 22b, 22c, 22d, 22e. An internal, open region 24 is disposed between the top surface 22a and side surfaces 22b, 22c, 22d, 22e. Canopy drape 22 preferably has a first thickness.

A vent portion or air intake portion 25 is provided through which fresh air may be passed into region 24. In a preferred, exemplary embodiment, portion 25 is a cut-out region of canopy drape 22 covered by gas-permeable media 25a. Preferably, gas-permeable media 25a for inlet air is formed of filter material that is a 0.5 inch thick, polyester plastic filter, McMaster-Carr Part No. 2182K51, which may be folded in half and upon itself so as to be about 6" by 12" and double-layered (about 1 inch thick). An appropriate material for inlet air filter 25a need not be particularly effective at trapping small particles, and importantly must not substantially reduce airflow into open region 24 as will be described in connection with creating a negative pressure therein and separately filtering air exhausted from open region 24. Thus, the preferred choice of inlet air filter 24 need not have a minimum efficiency rating value (MERV) rating. Gas-permeable media 25a preferably is selected so that, in combination with first and second filters 36a, 36b (which components will be described below), a flow rate of air from the internal, open region 24 of the canopy drape (and thus from external to enclosure 10 and into enclosure 10 through air intake portion 25) is possible between about 70 cubic feet per minute (cfm) and about 100 cubic feet per minute. Preferably, the combination of gas-permeable media 25a with first and second filters 36a, 36b permits a flow rate of air from external to enclosure 10 such that a negative pressure of at least 0.010 inches of water can be generated in the open, internal region 24 of enclosure 10, e.g. with a fan 38 (as described below). In one preferred exemplary embodiment, filters 25a, 36a, 36b permit a flow rate of air such that a negative pressure between about 0.010 and about 0.035 inches of water is achieved, more preferably 0.020 inches of water. In some embodiments, a negative pressure of at least 0.015 inches of water or at least 0.025 inches of water is achieved. In a preferred, exemplary embodiment, to facilitate replacement, gas-permeable media 25a is disposed in a pocket created between two pieces of 10 mil thick plastic such as the same material used for canopy drape 22.

A two-way, transfer chamber 27 preferably is coupled to at least one of side surfaces 22d, 22e proximate the region where a patient's head would be disposed. As is known in the glove box art, such an "airlock" for example may be box-like in overall shape and have an external access door 27a through which objects such as medications, syringes, stethoscopes, thermometers, ultrasound probes, etc. may be deposited into an internal region (airlock) of chamber 27 or alternatively retrieved therefrom, as well as a separate internal access door 27b through which such items may be transferred from the airlock to internal, open region 24 of enclosure 10 or alternatively from region 24 to the airlock. In a preferred exemplary embodiment, door 27a is formed by a zipper while door 27b is formed by a cross-shaped slit or a zipper. In one embodiment, transfer chamber 27 is formed of the same material and thickness (e.g., 10 mils) as canopy drape 22 so as to be generally rigid in order to maintain a box-like shape. In the exemplary embodiment, a single transfer chamber 27 is provided.

In the exemplary embodiment, canopy drape 22 is coupled to frame 16 via carabiners 26 which in turn are coupled to ties 28. Ties 28 are directly coupled to cross-members 20a, 20b while carabiners 26 are directly coupled to canopy drape 22 through grommets 30. In a preferred embodiment, grommets 30 are fabric grommets, McMaster-Carr Part Reference Number 96015K33, providing an internal opening with diameter 9.52±1 mm (0.38±0.4 inch). Grommets are sealingly associated with canopy drape 22 so as to be airtight. In the preferred embodiment, as shown for example in FIGS. 3-4, grommets 30 are spaced about the upper edges of side surface 22d and also side surface 22e. Preferably, five grommets 30 and five corresponding carabiners 26 are disposed on each of side surfaces 22d, 22e.

A pair of sleeves/gloves 32 are coupled to canopy drape 22 on each of sides 22a, 22e and protrude into open region 24 formed within canopy drape 22. Sleeves/gloves 32 are configured for receiving hands and arms of a user. Preferably, the sleeves are formed of a second polymeric material and have a closed, first free end 32a and an open, second free end 32b. Sleeves/gloves 32 preferably have a second thickness. In some embodiments, to facilitate ease of insertion of an HCP's hands and arms, sleeves/gloves 32 are formed of a material with a smooth surface. The sleeves/gloves 32 are coupled to canopy drape 22 to form an air-tight seal therebetween. In some embodiments, the sleeve portions are mechanically coupled to canopy drape 22, e.g., with mounting clamps. In other embodiments, the sleeve portions may be integrally formed with canopy drape 22, and in other embodiments, sleeve portions may be permanently coupled to drape 22 such as by heat welding, ultrasonic welding, bonding, stitching, and/or use of seam tape. In some embodiments, the sleeves and gloves are permanently fixed to each other, while in other embodiments they are demountably coupled to one another, e.g., especially so that gloves may easily be replaced.

In an exemplary embodiment, sleeves/gloves 32 have a thickness less than the thickness of canopy drape 22. At least four (4) pairs of sleeves/gloves 32 optionally may be provided.

Zippers 34 are disposed along side surfaces 22d, 22e, the zippers having a closed state and an open state. The zippers 34 are generally vertically oriented along substantially all of the width of the sides. When in the open state, the side surfaces are not folded about themselves, thus preventing contagions from spreading from inside enclosure 10 to the outer surfaces thereof. In the preferred exemplary embodiment, two zippers 34 are provided, one on each side surface 22d, 22e and preferably generally centered (lengthwise) along those sides as shown for example in FIG. 1.

A first filter 36a is disposed in communication with a second filter 36b. The filters 36a, 36b preferably are disposed on opposing surfaces of sides 22b of canopy drape 22. In the preferred, exemplary embodiment, filters 36a, 36b together provide high efficiency particulate air filtration to filter at least 99.97% of airborne particulate of 0.3 μm diameter. More preferably, filters 36a, 36b together provide high efficiency particulate air filtration to filter at least 99.997% of airborne particulate of 0.3 μm diameter.

Airborne particulate of particular relevance includes both acellular microorganisms (e.g., lacking cytoplasm or organelles, such as viruses, viroids, and prions) and cellular microorganisms (e.g., bacteria, fungi, and protozoan parasites). Thus, as used herein, the term "microorganism" includes both acellular and cellular microorganisms as just described.

The coronavirus SARS-CoV-2 has been characterized as involving generally spherical viral particles (with some pleomorphism) having a diameter from about 60 nm to 140 nm along with spikes projecting therefrom about 9 nm to 12 nm, thus giving the virions the appearance of a solar corona. See Zhu N, Zhang D, Wang W, et al. A Novel Coronavirus from Patients with Pneumonia in China, 2019. N Engl J Med 2020, 382(8):727-733.

*Mycobacterium tuberculosis*, a microorganism that is another airborne pathogen, also is known to be pleomorphic and varies in size and shape (often described as long rods but sometimes short rods or ovals) with the bacilli having a length of 1-10 μm (usually 3-5 μm) and a width of 0.2-0.6 μm. See, e.g., Velayati A A and Farnia P (2012). Morphological Characterization of *Mycobacterium tuberculosis*, Understanding Tuberculosis—Deciphering the Secret Life of the Bacilli, Dr. Pere-Joan Cardona (Ed.); Ufimtseva E, Eremeeva N, et al. *Mycobacterium tuberculosis* shape and size variations in alveolar macrophages of tuberculosis patients. European Respiratory Journal 2019 54: PA4605.

Nevertheless, the virion or bacterium size does not solely dictate the size of particle to be captured by a filtering system. Rather, the mode of airborne travel of the virion from an infected patient—coughs and sneezes, and indeed basic respiration, which create biological aerosols—largely sets the performance requirements for filtration media. See, e.g., Johnson G R, Morawska L. The Mechanism of Breath Aerosol Formation. J Aerosol Med Pulm Drug Deliv. 2009, 22:229-237. Such carrier aerosols can have particles several orders of magnitude larger than the virions themselves, with aerosol sizes extending to a supermicron diameter. See, e.g., Hsiao, T C, Chuang, H C, et al. COVID-19: An Aerosol's Point of View from Expiration to Transmission to Viralmechanism. Aerosol Air Qual Res 2020, 20:905-910 (noting that both droplets and droplet nuclei are considered to be aerosols); Han Z Y, Weng W G, Huang Q Y. 2013 Characterizations of particle size distribution of the droplets exhaled by sneeze. J R Soc Interface 10: 20130560.

A non-exhaustive list of pathogens that may spread via airborne transmission is: anthrax, aspergillosis, blastomycosis, chickenpox, adenovirus, enteroviruses, rotavirus, influenza, rhinovirus, *Neisseria meningitidis, Streptococcus pneumoniae*, legionellosis, measles, mumps, smallpox, cryptococcosis, tuberculosis, *Bordetella pertussis*, Severe Acute Respiratory Syndrome (SARS), Middle East Respiratory Syndrome (MERS), and Coronavirus Disease 2019 (COVID-19). See, e.g., Ather B, Mirza $T_M$, Edemekong P F. Airborne Precautions. [Updated 2020 Jun. 28]. In: StatPearls [Internet]. Treasure Island (FL): StatPearls Publishing; 2020 January-. Available from: https://www.ncbi.nlm.nih.gov/books/NBK531468/. Microorganisms transmitted by an airborne route may be spread, e.g., by aerosolization, during which microorganisms about 5 micrometers or smaller in size are contained in droplets that float in the air. Id.

An exemplary microorganism sized at about 20 nm is the rhinovirus.

In sum, the size of the virion or bacterium itself is not the only consideration with respect to desired filtration performance. Because viruses and bacteria become airborne on carriers during coughing, sneezing, vocalizing (e.g., speaking), or even simply when exhaling occurs, the sizes of the airborne carriers (containing the viruses and bacteria) must be considered as well.

Preferably, the filtration associated with enclosure 10 addresses the problem of aerosolization of pathogens, such as COVID-19 viral particles or *Mycobacterium tuberculosis*, during patient respiration, coughing, and sneezing, and substantially decreases airborne transmission thereof from region 24 within canopy drape 22 to HCP and others present outside enclosure 10 in the general vicinity of air exhausted from enclosure 10 due to necessary air exchange.

Advantageously, by placing filter 36a above the head of a subject 14 within enclosure 10, filter 36a is disposed close to the mouth and nose of subject 14 so that respiratory droplets (e.g., airborne particles) are drawn toward filter 36a prior to scattering elsewhere within enclosure 10.

A fan 38 in communication with filters 36a, 36b is used to create negative pressure in the internal region 24 of the canopy drape 22. Fan 38 is configured to evacuate air from internal region 24 through filters 36a, 36b. In the preferred embodiment, fan 38 is a Fantech Rn3 inline radon fan, which has the following specifications: 6 inch pipe; plastic housing; 2.6 inch max static pressure (SP); voltage (nominal) 120 V; frequency 60 Hz; phase(s) 1~; input power 141 W; input current 1.2 A; impeller speed 2,782 r.p.m.; air flow max 377.0 cfm; circular, inlet and outlet duct dimensions each 6 in.; and weight 6.3 lb. Fan 38 preferably is selected based on factors including cost, movability/portability (e.g., low weight), size to power ration, low noise, long lifetime (e.g., mean time to failure), and safety (e.g., providing a low risk of fire due to malfunction). Selection of a radon fan— traditionally used in active radon mitigation systems to exhaust radon gas from below buildings prior to migration into the building envelope—unexpectedly meets the aforementioned requirements in the unrelated application of a patient isolation system. Filters 36a, 36b, for example, may be RIDGID® VF6000 Hi-Efficiency Filters available, e.g., from hardware stores such as Home Depot as well as McMaster-Carr (Part Reference No. 14125T9). The VF6000 model is a 5-layer, cylindrical shaped replacement allergen cartridge filter made from HEPA-rated material and is typically used as the standard filter in wet/dry vacuum cleaners. The VF6000 has a diameter of about 6.25 to 7.30 inches and a length of about 8.75 to 9.30 inches.

Filter leak testing was performed for enclosure 10 with RIDGID® VF6000 Hi-Efficiency Filters for filters 36a, 36b, in accordance with Recommended Practice IEST-RP-CC034.4 (HEPA and ULPA Filter Leak Tests). The testing confirmed that, using this two-filter arrangement, the system attained a filtration efficiency greater than 99.999% for an average 0.3-micron size particulate.

Fan 38 preferably achieves a flow rate of air from the internal, open region 24 of the canopy drape (and thus from external to enclosure 10 and into enclosure 10 through air intake portion 25) between about 70 cubic feet per minute (cfm) and about 100 cubic feet per minute. In a preferred, exemplary embodiment, operation of fan 38 creates a negative pressure within region 24 of at least 0.010 inches of water, more preferably at least 0.020 inches of water, and most preferably between 0.010 inches of water and 0.035 inches of water. Advantageously, experimentation has demonstrated that fan 38 is relatively quiet for example when creating a negative pressure in region 24 of at least 0.020 inches of water. A potentiometer or variable speed control 43 may be used to adjust the speed of fan 38. Control 43, for example, may be a Fantech Model #WC 15 variable speed control (115 volts max.; 5 amps max.; 575 watts) allows for power adjustment of fan 38 as necessary. In an alternate embodiment, an adaptive feedback control system may be used to control the speed of fan 38 to automatically maintain a pre-set amount of negative pressure in region 24. Such a system would reduce the decision-making (and control) by HCP operating enclosure 10, simplifying its use as well as decreasing the risk of erroneous operation of enclosure 10. In some embodiments, a control system is employed with closed-loop fan speed control integrated circuits (FSC-ICs), while in other embodiments, open-loop fan drive ICs are used. Preferably, at least one sensor is used to measure pressure in region 24 and provides pressure measurements which then are used as feedback for a fan speed control algorithm with a pre-set, target pressure or pressure range for region 24.

In an exemplary embodiment, fan 38 is provided as part of a "Pre-Wired Rn3 Radon Fan System," available from Wholesale Radon (https://www.wholesaleradon.com/), with a fully-connected electrical box including a disconnect switch, along with a 6-foot cord with plug but without a power supply providing a speed control dial/capability.

In a preferred, exemplary embodiment, the HVAC system including fan 38 is able to create up to 100 air changes per hour in enclosure 10.

Air exchange rates, which may be referred to as air exchanges per hour or air changes per hour, refer to the number of times that air gets replaced in the internal region 24 each hour.

In some alternate situations, such as when it is necessary to protect a patient in enclosure 10 from the environment outside enclosure 10, e.g., a child who is immunosuppressed and being treated with chemotherapy, it is desirable to create a positive pressure within internal, open region 24. In other words, the environment outside enclosure 10 may have airborne particles which present a danger to the well-being of the patient in enclosure 10. In such situations, for example, fan 38 may achieve a flow rate of air from external to enclosure 10 first through filter 36b, then through filter 36a into the internal, open region 24 of the canopy drape 22 between about 25 cubic feet per minute (cfm) and about 100 cfm, and in some embodiments 70 cfm and about 100 cfm.

In a preferred, exemplary embodiment, operation of fan 38 creates a positive pressure within region 24 of at least 0.010 inches of water, more preferably at least 0.020 inches of water, and most preferably between 0.010 inches of water and 0.035 inches of water. In some embodiments, air from within enclosure 10 may be exhausted through portion 25 (serving as an exhaust portion instead of an intake portion) optionally covered by gas-permeable media 25a.

Advantageously, it is known that "a simple HEPA-rated filter will perform as an ULPA-rated or better filter by simply lowering the flow velocity through the media." Perry J L, Agui J H, & Vijayakumar R, Submicron and Nanoparticulate Matter Removal by HEPA-Rated Media Filters and Packed Beds of Granular Materials, NASA/TM-2016-218224, NASA, May 2016. Importantly, by setting a modest flow rate of air from the internal, open region 24 of the canopy drape 22 (and thus also from external to enclosure 10 and into enclosure 10 through air intake portion 25) to an external region of the canopy drape 22 between about 70 cfm and about 100 cfm, filters 36a, 36b are able to effectively filter airborne virion such as COVID-19 and bacterium such as *Mycobacterium tuberculosis*, especially on typical carriers. Optionally, an uninterrupted power supply (UPS) battery backup may be used to power fan 38. For example, a Schneider Electric APC Back-UPS Pro BX1000M-LM60 (AC 120 V; 600 Watt; 1000 VA) may be used.

In some embodiments, fan 38 and speed control 43 are demountably attached to patient support 12.

In some embodiments, fan 38 and speed control 43 are disposed remote from patient support 12, such as resting on a floor or otherwise disposed some distance away from patient support 12, even in a different room or setting from where the patient in enclosure 10 is located. In embodiments in which the outlet side of fan 38 is resting against a surface, cut-outs 38a may be provided in the housing thereof for purposes of air flow.

Tubing 44 connects housing 37 for filter 36b to canopy drape 22 proximate filter 36a. In a preferred, exemplary embodiment, tubing 44 is 3.5 feet long, lightweight, very flexible, and preferably 4 inch inner diameter. Suitable duct hose is available from McMaster-Carr, part reference number 5488K63, ribbed tubing with a 0.5 inch bend radius, specified for a maximum vacuum of 6.5 in. of Hg at 72° F. and a maximum pressure of 5 psi at 72° F.

Preferably, filter 36a disposed in the internal region 24 is provided with an adaptor, collar, or other suitable coupling 39 at one end thereof proximate canopy drape 22 while tubing 44 also is provided with an adaptor, collar, or other suitable coupling 41 at one end thereof proximate canopy drape 22. In an exemplary embodiment, couplings 39, 41 are magnetically attracted to one another so that when aligned with respect to each other, such as along axis $A_1$, they securely seal against canopy drape 22 on either side thereof. A hole in canopy drape 22 preferably is sized to permit passage of air from filter 36a through tubing 44. Advantageously, with couplings 39, 41, air that has passed through filter 36a is directed into tubing 44 without leaking. Such an arrangement may facilitate rapid changes of filter 36a.

A negative pressure indicator 40 is provided internal to enclosure 10. Indicator 40 is a balloon-like, flexible membrane coupled to canopy drape 22. In a preferred, exemplary embodiment, indicator 40 is generally flaccid when uninflated and rectangular shaped when inflated either by negative pressure such that indicator 40 protrudes toward the interior of enclosure 10 or positive pressure such that indicator 40 protrudes toward the exterior of enclosure 10.

Figure 9C:
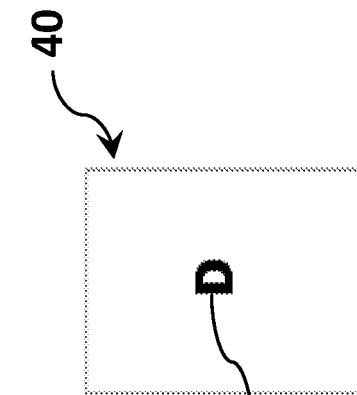
Figure 9B:
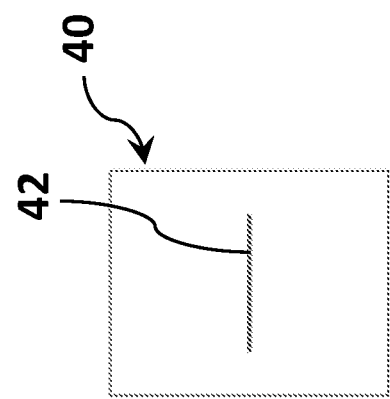
Figure 9A:
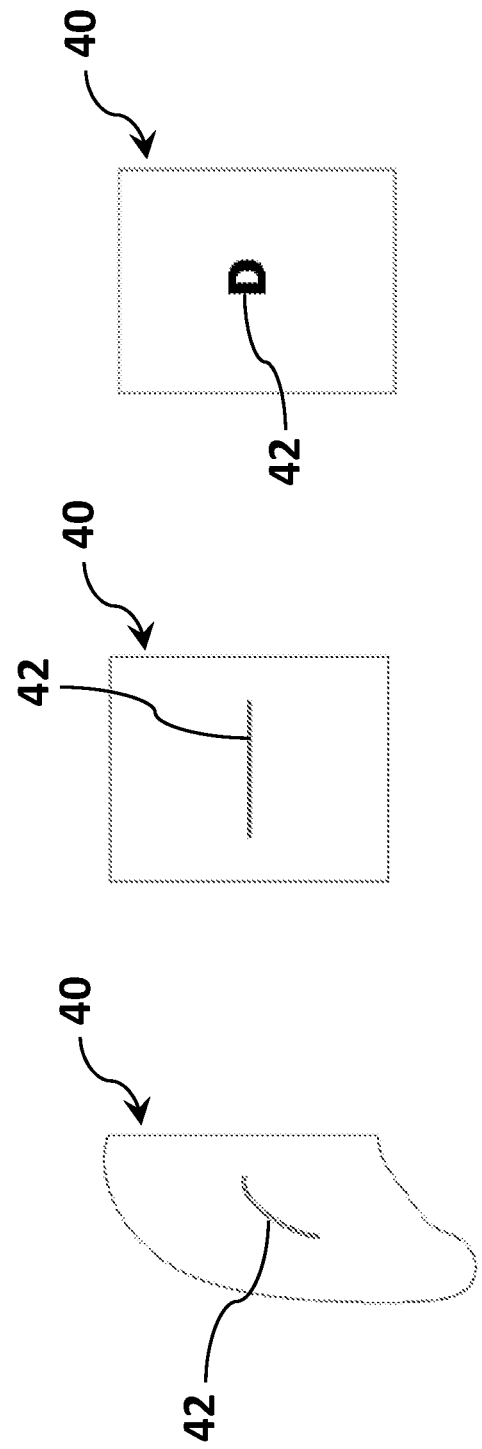
Figure 10:
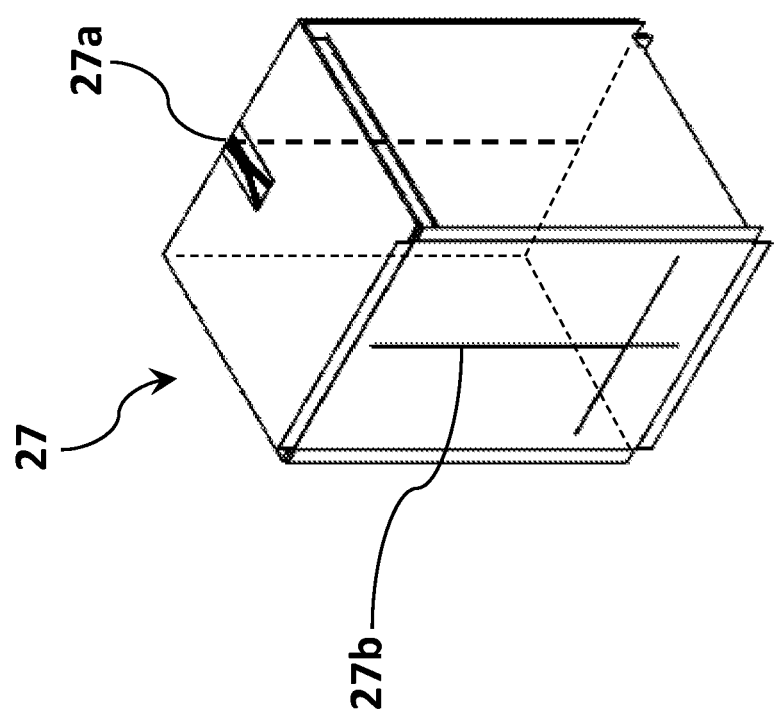
Figure 11:
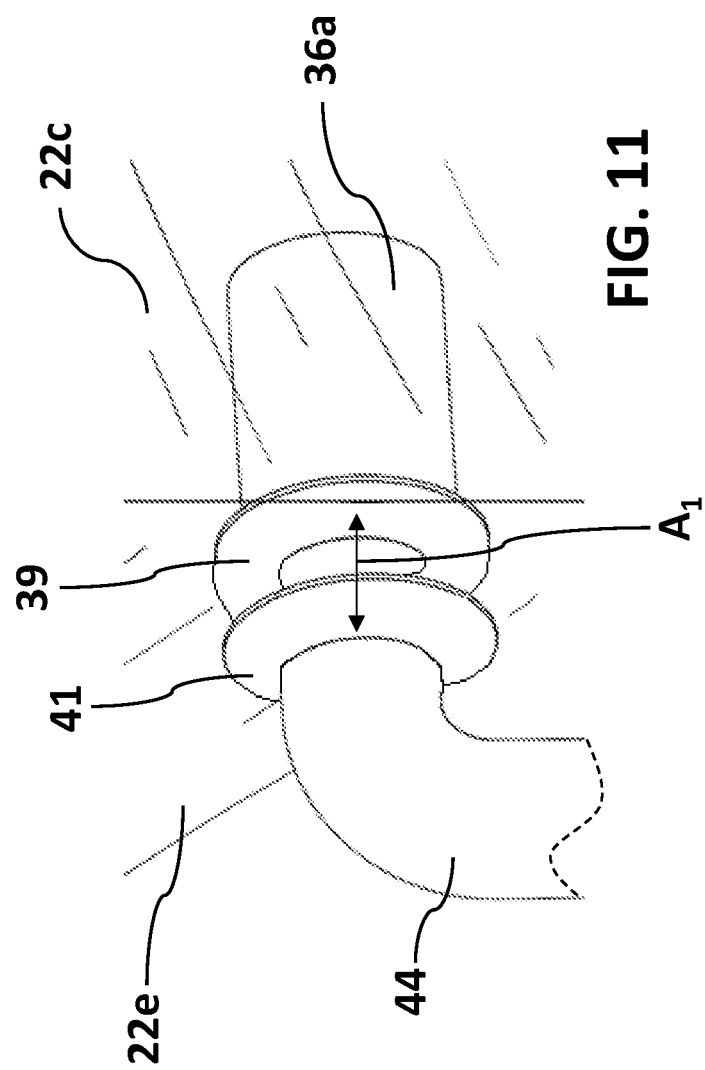

Indicia 42 may be provided, such as a line that in the preferred embodiment becomes straight and generally horizontally aligned when indicator 40 is substantially fully inflated as shown in FIG. 9A and FIG. 9B. In another exemplary embodiment, indicia 42 may be a geometric shape such as a letter "D" or a logo, as shown for example in FIG. 9C.

In a preferred, exemplary embodiment, canopy drape 22 is formed of 10 mil thick thermoplastic polyurethane (TPU), Polyzen Part No. TSP-1058-0090. For a standard size, emergency department bed, canopy drape 22 may have overall dimensions on its top surface 22a of 800 mm (31.49 inches) between side surfaces 22d, 22e (e.g., from the left hand side to the right hand side of the bed), 2000 mm (78.73 inches) between side surfaces 22b, 22c (e.g., from the head to foot of the bed), and side surfaces 22b, 22c, 22d, 22e may have a height of 1219 mm (48 inches). For a standard size, intensive care unit (ICU) bed, canopy drape 22 may have overall dimensions on its top surface of 926 mm (36.46 inches) between side surfaces 22d, 22e (e.g., from the left hand side to the right hand side of the bed), 2200 mm (86.61 inches) between side surfaces 22b, 22c (e.g., from the head to foot of the bed), and side surfaces 22b, 22c, 22d, 22e may have a height of 1700 mm (66.93 inches). The type and especially thickness of polymer used to form canopy drape 22 can impact the transfer of sound to and from the patient, and thus preferably the polymer is selected so as not to substantially muffle sounds. In some embodiments, top surface 22a is 800 mm to 1000 mm between side surfaces 22d, 22e, 2000 mm to 2200 mm between side surfaces 22b, 22c, and side surfaces 22b, 22c, 22d, 22e may have a height of 1100 mm to 1800 mm.

In a preferred, exemplary embodiment, the gloves/sleeves 32 are formed of Polyzen Part No. 510511 using Polyzen material SIP-368, corresponding to Polyzen's polyether polyurethane 90A film. The sleeves and gloves preferably are 2 mil thick may have an overall length of 873.90±10.00 mm (34.41±0.39 inches). The sleeves themselves preferably may be frustoconical with an overall length preferably of 620 mm (24.41 inches), a diameter proximate coupling to the gloves of 97.03 mm (3.82 inches), and a diameter proximate coupling to the canopy drape of 220 mm (8.66 inches) or an ellipse with a height of 20 inches. Gloves/sleeves 32 preferably have a thickness that permits them to expand slightly under the negative pressure created within internal, open region 24 of canopy drape 22; in other words, gloves/sleeves 32 cannot be too thick/heavy and preferably extend within region 24 when there is negative pressure therein. When not in use, gloves/sleeves 32 preferably are disposed to extend outside region 24 (e.g., a user turns them inside out by pulling them outside of canopy drape 22, so that gloves/sleeves 32 do not interfere with the patient in enclosure 10. In one embodiment, enclosure 10 is provided with four pairs of gloves/sleeves 32, which may be disposed at any of side surfaces 22b, 22c, 22d, 22e.

In some embodiments, the tent has a lightweight frame 16 and a clear covering 22. The frame can be made, for example, of plastic (e.g., PVC pipe), metal (e.g., aluminum), or any other suitable material. The covering may be, for example, a plastic sheet or tarp. In an exemplary embodiment, the tent may be formed of thermoplastic polyurethane (TPU). The tarp can optionally be a lightweight, transparent plastic material that is resistant to static electricity (e.g., anti-static or static-dissipative). The material of the covering can be selected to maximize efficiency of clinical care through attached amenities. The covering can be attached to the frame by any suitable method. In some embodiments, the cover is draped over the frame. It can be held in place by gravity, by folding or forming to a shape that corresponds to the frame, or via additional attachment features (e.g., clips, hooks, hangers, hook-and-loop surfaces, etc.). Alternately, the cover can be suspended from the frame using similar types of attachment features.

In some embodiments, a negative pressure is maintained inside the chamber region formed by the tarp. This can be accomplished using a filtering and/or ventilation system. The system can be a customized system, a conventional system designed for clinical use, or it can be a low-cost system made of off-the shelf, non-medical components.

In an exemplary embodiment, the filtering system includes a small (e.g., approximately 6-12 inch) motorized fan, which is contained in a housing outside the isolation tent. The housing can be mounted onto existing features of a hospital bed. Additionally, the fan housing can be located at any position along the periphery of the bed (e.g., placed on the floor of the room). For example, the fan may be located at the foot of the bed, or in a preferred embodiment may be located at the head. The fan is connected to the isolation tent by a modular length of tubing, and the tubing is connected to the cover in an airtight seal. A first filter is disposed at the terminal end of the tubing, optionally inside the isolation tent. A second filter is optionally located between the tubing and the fan.

The filter(s) can be either medical-grade filters (e.g., a high-efficiency particulate air, or HEPA, filter) or commercial grade filters. A study conducted by the inventors found that inserting two conventional "vacuum cleaner" style filters upstream of the fan achieves a filtration rate comparable to a HEPA filter. With this unexpected result, it has further been determined that it is possible to contain the virus/pathogen particles in the filters and tubing, without contaminating the fan components. Thus, the filtration system can be designed such that the tubing and filters are disposable, and the fan portion is reusable. This also allows for further processing of the filters to facilitate diagnosis of patients infected from unknown or difficult-to-isolate pathogens. In other words, filters may be removed and provided to a laboratory for analysis of pathogens collected therein.

Advantageously, portable protective enclosure 10 can be effectively and efficiently used for virus containment, delivery of care, and transport for COVID-19 patients. Enclosure 10 has an elegant design, and it is easy to assemble, clean, and use. In addition, enclosure 10 provides security to both patient and provider by providing an additional layer of protection; providers may potentially decrease Powered Air Purifying Respirator (PAPR) usage as some tasks can be carried out through glove and transfer boxes coupled to canopy drape 22. Advantageously, the design of enclosure 10 addresses concerns of overheating, as well as aerosolized virus and subsequent condensation on drape 22. The elegant design in particular facilitates rapid introduction and widespread usage of enclosure 10 by nurses and other healthcare professionals who must become accustomed to completing patient checks while a subject is isolated within enclosure 10.

Portable protective enclosure 10 is suitable for use during COVID-19 patient care, and its use for example facilitates the transfer of patients between rooms, provides a "sense of safety" to HCP, provides safe and easy access to a patient through zippers (such as four) and glove boxes (such as six), and may even save time in some emergent situations. While each enclosure 10 is meant to isolate a single patient, multiple enclosures 10 each with a patient can be placed in the same room so that like-patients may be clustered.

With respect to patient care, enclosure 10 employs transparent plastic thereby allowing for easy visibility of the patient by HCP. Moreover, the use of transparent plastic for canopy drape 22 can be reassuring to a patient housed within enclosure 10 so that the patient can view activities, as well as HCP and others, who are outside enclosure 10. Without such transparency, a patient may become nauseated or otherwise feel uncomfortable (e.g., isolated, confined, claustrophobic), particularly when attempting to focus on people or objects outside enclosure 10. Still further, transparency permits HCP to perform certain close-up checks of a patient, such as pupillary assessment involving observations of changes in the size, equality and reactivity of a patient's pupils. Transparency also permits a patient to view entertainment (e.g., a television) which can impact mental health.

The sleeves/gloves 32 coupled to canopy drape 22 also permit patients to have indirect physical contact with family members or HCP, with potential mental health advantages. Such sleeves/gloves 32, along with transfer boxes, can permit HCPs to measure vital signs of a patient, insert intravenous and central lines, manipulate ventilation tubes, use ultrasound equipment, and use a stethoscope. The one or more zippered regions provided on enclosure 10 also allow quick access to the patient as may be necessary. In an exemplary embodiment, the system includes a filter 36a that attaches to the inside of the isolation tent through a press fit mechanism. This filter 36a is then connected to corrugated tubing 44, which guides the air out of the chamber to the main body of the device. The main body contains an identical secondary filter 36b housed, for example, inside a PVC cylinder, through which the air is drawn before reaching the powered fan 38. The fan can optionally be a radon mitigation style fan, which has a sealed housing. The housing for the secondary filter is attached to the tubing and the fan with adjustable pipe couplings. Connected to the side of the PVC cylinder and the top of the fan is a mounting bracket designed to attach to multiple types of hospital beds, to provide universal hospital bed adaptation. Alternate attachments can be substituted or added to accommodate hospital bed types of varying dimensions. While the HVAC system is capable of continuous operation when connected to wall power, an optional power storage solution allows for portable short-term use during transportation. The device is further configured to allow placement directly on the floor while in use, allowing for additional space surrounding the bed. This is useful, for example, for various medical procedures and operations. The shape, size, and weight of the HVAC system allows medical professionals to attach or remove the device from the bed quickly with minimal effort, and an air-tight press-fit connection of the vacuum hose to the interior initial filter allows for seamless connection and removal of the entire system from the bed and connected tent.

The frame can be designed such that it universally fits on substantially all hospital beds, emergency medical services (EMS) stretchers, emergency department (ED) stretchers, and beds in low-resource settings. The frame is collapsible and adaptable to the hospital bed or to a stretcher. In a non-limiting exemplary embodiment, the frame can be a scissors-style foldable frame that has mounting features at the bottom of the frame for attaching to a bed or gurney. This allows healthcare professionals to move the bed while the device is installed. The mounting features can be designed to interface with existing bed features, such as a rod and socket device. To insert the device, the scissors or X-frame can be opened and inserted into mating receptacles on the bed. To remove it, the frame is lifted up and folded closed.

The tent optionally includes one or more glove boxes or sleeves, slits, pockets, two-way (delivery) boxes, zippers, and/or other features that will be evident to a person of skill in the art. Multiple such features can be located in any surface of the device. Many treatment functions—such as checking vital signs, installing ventilation tubes, connecting intravenous drips, administering medication, and installing and connecting leads such as for cardiac monitoring—can be performed across the barrier via the gloves or sleeves. The device can further be equipped with features to hold open "curtains" of the enclosure; in other words, when a side is opened to permit access such as through a zipper—for example if more invasive procedures are required—the opposing edges of the zipper may be held apart from each other in an open state.

The device is simple, inexpensive, and easy to assemble, clean, and use. It provides security to both patient and provider by having an additional layer of protection. It may potentially decrease the need for PPE and/or PAPR usage, as almost all clinical tasks can be carried out through the glove boxes. Further, it can be used to provide isolation when transferring patients between locations. In some cases, it may provide a "sense of safety" for healthcare providers, patient relatives, and visitors. A tent as disclosed herein can potentially decrease the number of ventilators needed for infectious patients by increasing the ability of healthcare providers to use non-invasive ventilation methods (e.g., BiPAP, CPAP, etc.) without increasing their risk of infection. The use of non-medical filters to accomplish a HEPA-level filtration rate can potentially decrease the amount of HEPA medical filters needed during a pandemic, when a shortage of such filters is common. Additionally, processing of the filters (e.g. with metagenomics or with any other laboratory technique) may be used to facilitate diagnosis of housed infectious patients. Ease of use and clean-up are facilitated because some components of enclosure 10 are disposable.

The following Examples are provided by way of illustration and not by way of limitation.

EXAMPLES

I. Prototype Results

1. Negative pressure and stable temperature can be maintained inside the isolation tent by using a simple HVAC system and achieving a HEPA filtration rate (>99.97% and preferably >99.997% filtration at 0.3 microns) with non-HEPA filters that are readily available (vacuum cleaner filters). That is extremely important in cases such as the COVID-19 pandemic, during which medical filters are in short supply. This also can be achieved with a portable device which can be easily deployed in every setting, thus substantially increasing isolation room capacity in every hospital. Unexpectedly, the use of non-medical filters is capable of achieving that level of filtration.

The pressure within the tent can be monitored through a pressure-monitoring system on the device, which highlights a satisfactory steady-state range for the system, which was experimentally determined to be between 0.01 and 0.035 inches of $H_2O$. The pressure monitoring system can be passive, inasmuch as an expandable vessel such as a balloon-like protrusion may be attached to a portion of the tarp and when negative pressure is achieved, it may inflate inwardly and include indicia such as a line indicating when proper pressure is present such as when the line is disposed generally parallel to the ground upon full inflation of the expandable vessel. All connections from the initial filter to the ultimate fan outlet are completely air-tight, with the only exhaust air coming from the bottom of the fan, which was verified as particulate-free air during experimentation.

2. This device is designed to work in every clinical setting. It can be used for transportation of patients (EMS, life flight, inside the hospital or nursing home), isolation in rooms (regular or ICU) and isolation in large spaces (i.e. when housing several patients in surge facilities). Notably, it can also be used in low-resource settings. This makes it a viable business proposition and opportunity regardless of whether it is to be used during a pandemic or during other, more stable times.

3. The device provides the ability to increase utilization of non-invasive ventilation methods (e.g., BiPAP, CPAP, etc.) to support the respiratory system of infected individuals, thus minimizing the number of ventilators that are required to be used and this can be done in a manner that is safer for the staff. This is highly significant, for example, in a pandemic where shortage of ventilators is a reality.

4. The device provides the ability to minimize usage of personal protective equipment (PPE) from HCP when they take care of infected patients which is also very significant due to the PPE shortage.

5. Processing of the filters (e.g., with metagenomics or any other laboratory technique), may be used to facilitate diagnosis of housed infectious patients.

II. Exemplary Assembly

Exemplary assembly instructions for the isolation tent frame are as follows:

1. Placement of zip ties and carabiners.
2. Place 5 zip ties and carabiners on one side bar and 5 zip ties and carabiners on the other side bar of the frame.
3. Two people should lift and move the frame so that the marked head and foot are in the correct orientation and align with the bed; each person should lift the frame from the cross-section area.
4. Place the frame in the head and foot holes found at both ends of the bed.
5. Ensure that the frame is sitting securely in these holes and that the frame supports are as deep as they can go in the holes.

III. Exemplary Assembly Instructions for Isolation Tent HVAC System

1. When securing the HVAC system on an ED stretcher, gather the supplies for the mounting bracket of the HVAC system. When securing to a regular floor or ICU bed, go to step 6. A wrench is needed for the assembly.
2. Place the square metal bar on the cylinder metal bar of the head frame of the ED stretcher. Place the plastic face facing you.
3. Place the metal place with the two holes over the U bolt.
4. Screw the two nuts to the U bolt. Use the wrench to tighten them.
5. Place the rubber caps over the U bolt.
6. Place the fan and hose over the bracket of the ED stretcher, regular floor bed, or ICU bed. Mount the HVAC system at the center of the headboard of the bed with the channel-shaped mounting part. The HVAC system should face outwards.

IV. Exemplary Assembly Instructions for Isolation Tent

1. Unfold the tent.
2. Align the tent in proper orientation with having the prefilter at the foot.
3. Attach the tent to the carabiners through the grommets. Repeat 10 times for each grommet/carabiner interface.
4. Tighten the zip ties to secure the carabiners at the desired position on the frame.
5. Placed tent should be fully expanded and in the desired position.
6. Place the sleeves on the outside of the tent.
7. Attach interior HEPA filter by opening the tent and placing the back of the filter (the side with a connection attachment) through the marked hole in the tent above the head of the bed. Place the clear, plastic attachment around the part of the HEPA filter and tent cover flaps protruding on the outside of the tent.
8. Attach the hose from the HVAC device onto the outside of the HEPA filter. Ensure a tight seal by pushing the HEPA filter as close to the hose as possible until it clips into place; make sure holes clip into each other at connection point.
9. Fully close all zippers (sides and two-way access box zippers)
10. In some embodiments, tuck in the tent under and completely around the mattress of the bed. The side zippers can be opened to mattress level. In other embodiments, tucking of the tent under the mattress is not needed.
11. Place battery backup on bottom framework of the bed.
12. Plug the HVAC system into any of the "Battery Backup" outlets of the battery supply included in the parts
13. Plug the battery backup into an outlet.
14. Turn the fan on by setting the dial at the bottom of the fan to HIGH.
15. Test the system by letting the fan run for a few minutes and visually inspect the tent for hour-glass shape.

One skilled in the art will readily appreciate that the disclosure herein is well adapted to carry out the objects and obtain the ends and advantages mentioned, as well as those inherent therein. The disclosure herein includes representative, preferred embodiments that are exemplary and are not intended as limitations on the scope of the disclosure. Changes to the exemplary embodiments and other uses will occur to those skilled in the art and are encompassed within the spirit of the disclosure herein as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The disclosure herein shall control in the event there are any disparities between any definitions and/or description found in the cited references.

The invention claimed is:

1. A portable, protective enclosure for coupling to a patient support for supporting a mammal comprising:
   a collapsible frame comprising a pair of X-shaped linkages coupled with a pair of cross-members;
   a canopy drape formed of a transparent, first polymeric material, the canopy drape being bottomless and having a top surface, a plurality of side surfaces, an internal region disposed between the top and side surfaces, an air intake portion, and a first thickness, wherein the canopy drape is coupled to at least one of the cross-members;
   a pair of sleeves and gloves configured for receiving hands and arms of a user, the sleeves and gloves together having a closed, first free end, an open, second free end, and a second thickness, wherein the sleeves are coupled to the canopy drape to form an air-tight seal therebetween and the second thickness is less than the first thickness;
a zipper disposed along one of the side surfaces, the zipper having a closed state and an open state, wherein the side surface is not folded about itself when the zipper is in the open state;
a first filter disposed in communication with a second filter, the first and second filters disposed on opposing sides of one of the side surfaces of the canopy drape, wherein the first and second filters together provide high efficiency particulate air filtration to filter at least 99.97% of airborne particulate of 0.3 μm in diameter;
gas-permeable media disposed in communication with and proximate the air intake portion;
a movable fan in communication with the first and second filters for creating a negative pressure of at least 0.01 inches of water in the internal region of the canopy drape, the fan configured to draw in air through the gas-permeable media into the internal region and evacuate air from the internal region through the first and second filters; and
a negative pressure indicator.

2. The enclosure of claim 1, wherein the first polymeric material is thermoplastic polyurethane and the first thickness is 10 mils.

3. The enclosure of claim 1, wherein at least one of the sleeves and the gloves is formed of a second polymeric material, the second polymeric material is thermoplastic polyurethane and is transparent, and the second thickness is 2 mils.

4. The enclosure of claim 3, wherein the negative pressure indicator comprises an expandable vessel coupled to the canopy drape and the expandable vessel is formed of the second polymeric material.

5. The enclosure of claim 1, wherein the sleeves are coupled to the canopy drape by a coupling selected from the group consisting of welds, bonds, or mechanical connections.

6. The enclosure of claim 5, wherein the coupling further comprises seam tape.

7. The enclosure of claim 1, wherein a plurality of grommets are disposed proximate the top surface of the canopy drape.

8. The enclosure of claim 1, wherein the canopy drape is coupled to both of the cross-members.

9. The enclosure of claim 1, wherein the fan provides a flow rate of air from the internal region of the canopy drape of between 70 cfm and 100 cfm.

10. The enclosure of claim 1, further comprising a control system to maintain the negative pressure of at least 0.01 inches of water in the internal region.

11. The enclosure of claim 1, wherein the internal region has a volume of between about 25 cubic feet and about 125 cubic feet.

12. The enclosure of claim 1, wherein the negative pressure indicator comprises an expandable vessel coupled to the canopy drape.

13. The enclosure of claim 12, wherein the expandable vessel comprises indicia for indicating when desired pressure is reached.

14. The enclosure of claim 12, wherein the expandable vessel is sealingly coupled to a side surface of the canopy drape.

15. The enclosure of claim 1, wherein the first and second filters together provide high efficiency particulate air filtration to filter at least 99.99% of airborne particulate of 0.3 μm in diameter.

* * * * *